United States Patent [19]
King et al.

[11] Patent Number: 5,929,319
[45] Date of Patent: Jul. 27, 1999

[54] BREATH TESTING APPARATUS

[75] Inventors: Paul King; Jason Aspinall, both of South Glamorgan, United Kingdom

[73] Assignee: Lion Laboratories Plc, South Glamorgan, United Kingdom

[21] Appl. No.: 08/981,158

[22] PCT Filed: Jun. 14, 1996

[86] PCT No.: PCT/GB96/01419

§ 371 Date: Dec. 17, 1997

§ 102(e) Date: Dec. 17, 1997

[87] PCT Pub. No.: WO97/00443

PCT Pub. Date: Jan. 3, 1997

[30] Foreign Application Priority Data

Jun. 17, 1995 [GB] United Kingdom ............... 9512396

[51] Int. Cl.[6] .................................................. G01N 33/497
[52] U.S. Cl. ........................... 73/23.3; 73/1.03; 73/1.06; 422/84; 436/132; 436/900
[58] Field of Search ..................... 73/23.3, 1.02, 73/1.06, 1.03; 422/84; 436/132, 900

[56] References Cited

U.S. PATENT DOCUMENTS

| | | | |
|---|---|---|---|
| 3,877,291 | 4/1975 | Hoppesch et al. ................... | 73/23.3 |
| 3,966,579 | 6/1976 | Chang et al. ........................ | 204/406 |
| 4,749,553 | 6/1988 | Lopez et al. ........................ | 422/84 |

FOREIGN PATENT DOCUMENTS

| | | | |
|---|---|---|---|
| 3403450 | 8/1984 | Germany ........................ | 73/23.3 X |
| 22813 | 12/1992 | WIPO .............................. | 422/84 |

OTHER PUBLICATIONS

Maksimovich et al., "Device with Semiconductor Gas Sensor for Alcohol Vapour Detection in an Exhaled Air Sample", Sensors and Actuators B, vol. B13, No. 1/3, May 1993, pp. 256–258.

*Primary Examiner*—Daniel S. Larkin
*Attorney, Agent, or Firm*—Young & Thompson

[57] ABSTRACT

This invention consists of breath testing apparatus 10 comprising a breath tube 11, a fuel cell housing 12 incorporating a pump system 12a, a fuel cell 13, a control and computational unit 14, and a display 15. A thermistor 22 is provided to detect the temperature of the housing 12 during measurement and the unit 14 compensates the fuel cell output in accordance with the detected temperature.

11 Claims, 1 Drawing Sheet

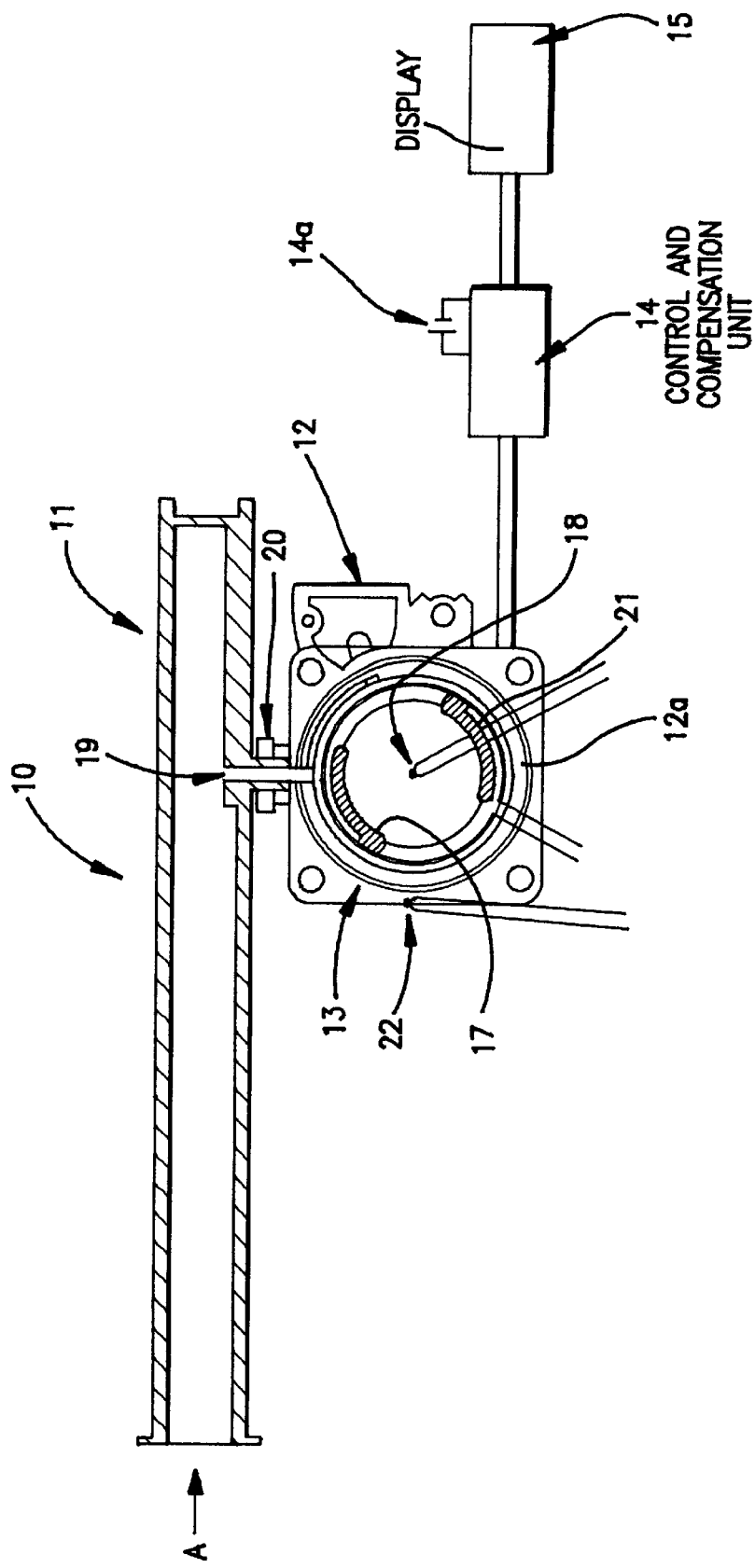

BREATH TESTING APPARATUS

FIELD OF THE INVENTION

This invention relates to breath testing apparatus for detecting volatile components, such as ethanol, in a subject's breath by oxidizing them in a fuel cell.

BACKGROUND OF THE INVENTION

Such apparatus is frequently used out in the open and may therefore have to operate in a wide range of temperatures. It is known that the fuel cell response is affected by temperature and attempts have been made to overcome this variation by heating the fuel cell so that it sits at or above a predetermined temperature by using thermistor control. However, this approach can cause problems both due to signal noise created by the heater and because it is difficult for the batteries in portable devices to supply sufficient current to run both the heater and the electronics associated with the fuel cell during the actual measurement process.

SUMMARY OF THE INVENTION

According to one aspect, the present invention consists in a breath testing apparatus including a fuel cell for producing an output signal, a housing for the fuel cell, a breath sampling means connected to the housing for drawing a breath sample into the fuel cell, a thermistor for detecting the temperature of the housing, compensation means for correcting the output signal of the fuel cell in accordance with the temperature detected by the thermistor, and means for displaying the corrected signal.

The apparatus may further include a heater, disposed within the housing, a thermistor for controlling the heater to maintain a part of the housing, adjacent the fuel cell, at or above a predetermined temperature, and means for disabling the heater during the operation of the fuel cell. The predetermined temperature is selected by the user based on conventional operating characteristics of the fuel cell and desired response set point of the heater. The thermistor for controlling the heater may also constitute the thermistor for detecting the temperature of the housing. The heater may be in the form of a coil or disc and the temperature-controlling thermistor may be disposed at or adjacent the center of the coil or disc.

The compensation means may include means for computing the corrected output of accordance with the following formula:

$$BAC_c = BAC_A \times \frac{A}{B + Cx - Dx^2}$$

wherein $BAC_C$ is the corrected Breath Alcohol Concentration $BAC_A$ is the actual Breath Alcohol Concentration measured by the fuel cell;

A is the concentration of the ethanol solution used to calibrate the fuel cell;

B,C+D are constants characteristic of the fuel cell being used and of its housing; and x is the temperature detected.

From another aspect, the invention consists of a method of operating a breath testing apparatus having a fuel cell in a fuel cell chamber, including detecting the temperature of the fuel cell chamber at the time the fuel cell is operational, calculating a correction factor in accordance with the temperature, applying the correction factor to the output of the fuel cell, and displaying the corrected output.

The correction factor may be:

$$\frac{A}{B + Cx - Dx^2}$$

wherein A is the concentration of the ethanol solution used to calibrate the fuel cell;

B,C, and D are constants characteristic of the fuel cell being used and of its housing; and x is the temperature detected.

The method may include the step of calibrating the fuel cell with a "wet" standard (e.g. one in which the calibration gas is an ethanol vapour generated by bubbling as though an ethanol standard) and the fuel cell may be heated. In this latter case, the heater may be switched off when or just before a sample is supplied to the fuel cell.

From a further aspect, the invention consists in a method of calibrating a breath testing apparatus having a fuel cell including supplying a "wet" standard and compensating the resultant output of the fuel cell in accordance with the temperature of the fuel cell or a housing containing it.

Although the invention has been defined above it is to be understood that it includes any inventive combination of the features set out above or in the following description.

The invention may be performed in various ways and a specific embodiment will now be described by way of example with reference to the accompanying drawing which is a schematic diagram of breath testing apparatus.

BRIEF DESCRIPTION OF THE DRAWING

The single drawing FIGURE illustrates the breath testing apparatus of the invention.

DESCRIPTION OF THE PREFERRED EMBODIMENT

Referring to the drawing, the breath testing apparatus, generally indicated at 10, comprises a breath tube 11; a fuel cell housing 12, incorporating a pump system 12a of the type made by Lion Laboratories Plc and supplied, for example, in their 400 Series machines for drawing a breath sample from the tube into the housing; a fuel cell 13; a control and computational unit 14, and a display 15. On the outside of fuel cell 13 there is a heater disc 17 and a thermistor 18 is disposed approximately at the centre of the heater 17. Both of these are connected to a power supply 14a associated with the unit 14.

As is well-known the user blows into the breath tube 11 in the direction marked by the arrow A and after a predetermined time of breath being blown above a predetermined pressure, a sample of breath is sucked down by the pump 12a into the housing 12 through a side port 19 formed in the breath tube 11 and an inlet 20 formed on the housing 12. This sample is then sucked into the fuel cell at 21. The fuel cell 13 oxidizes any ethanol in the sample, in a conventional manner, and its electrical output is fed to the control and computational unit 14.

It has been determined that the output of the fuel cell varies with temperature and this can be significant because the apparatus may be used in temperatures in a range which may be typically –5° C. to 40° C. The traditional approach to this is to heat the fuel cell housing, but this has the disadvantages previously noted. In the Applicant's arrangement, therefore, a temperature sensing thermistor, which is either constituted by the thermistor 18 or a distinct separate thermistor such as is illustrated at 22, is provided. This measures the housing temperature at the time that the fuel cell is operational and feeds this output to the unit 14, which then corrects the fuel cell output in accordance with the measured temperature before the output is displayed digitally to show the breath alcohol content (BAC) of the user. As the heater 17 is usually switched off during the operation of the fuel cell, both to prevent noise and battery drain, the thermistor 18 can provide this function for most purposes. If, however, it is desirable to run the heater during this operation, the separate thermistor 22 is to be preferred.

Experiments have shown that for fuel cells of the type WR manufactured by Lion Laboratories Plc, the computational unit provides an accurate output for display if it corrects the actual output in accordance with the following formula:

$$BAC_c = BAC_A \times \frac{A}{B + Cx - Dx^2}$$

wherein $BAC_C$ is the corrected Breath Alcohol Concentration $BAC_A$ is the actual Breath Alcohol Concentration A is the concentration of the ethanol solution used to calibrate the fuel cell;

B,C+D are constants characteristic of the fuel cells being used and of its housing; and x is the temperature detected.

It is anticipated that most fuel cells will have a correction formula of a similar form, but the constants will vary depending on the fuel cell and the housing. The appropriate constants can readily be calculated by one skilled in the art plotting the output of any particular fuel cell against temperature. It is perfectly possible with this arrangement to dispense with the heater altogether or to configure the arrangement such that the heater only operates if the fuel cell temperature is below say −5° C.

The Applicants have determined that, surprisingly, there is a difference in the temperature response of such breath testing apparatus to dry calibration samples as against wet calibration samples. The dry calibration samples, which are often provided in aerosol form, provide an inaccurate representation of the performance of the fuel cell against temperature and, contrary to normal practice, temperature compensation for breath testing apparatus of this sort should be calculated using a wet standard. This is the type where the calibration gas is in equilibrium with a liquid such as water.

What we claim is:

1. Breath testing apparatus including a fuel cell for producing an output signal, a housing for the fuel cell, a breath sampling means connected to the housing for draining a breath sample into the fuel cell, a thermistor for detecting the temperature of the housing, compensation means for correcting the output signal of the fuel cell in accordance with the temperature detected by the thermistor, and means for displaying the corrected signal.

2. Apparatus as claimed in claim 1, further including a heater, disposed within the housing, a thermistor for controlling the heater to maintain a part of the housing adjacent the fuel cell at or above a predetermined temperature and means for disabling the heater during operation of the fuel cell.

3. Apparatus as claimed in claim 2, wherein the thermistor for controlling the heater also constitutes the thermistor for detecting the temperature of the housing.

4. Apparatus as claimed in claim 2, wherein the heater is in the form of a flat coil or disc and the temperature controlling thermistor is disposed at or adjacent the center of the coil or disc.

5. Apparatus as claimed in claim 1, wherein the compensation means includes means for computing the corrected output in accordance with the following formula:

$$BAC_c = BAC_A \times \frac{A}{B + Cx - Dx^2}$$

wherein $BAC_C$ is the corrected Breath Alcohol Concentration $BAC_A$ is the actual Breath Alcohol Concentration measured by the fuel cell;

A is the concentration of an ethanol solution used to calibrate the fuel cell;

B,C+D are constants characteristic of the fuel cell being used and of a housing of the fuel cell; and x is the temperature detected.

6. A method of operating a breath testing apparatus having a fuel cell in a fuel cell chamber including detecting the temperature of the fuel cell chamber at the time the fuel cell is operational, calculating a correction factor in accordance with the temperature, applying the correction factor to an output of the fuel cell, and displaying the corrected output.

7. A method as claimed in claim 6, wherein the correction factor is $$\frac{A}{B + Cx - Dx^2}$$

wherein A is the concentration of an ethanol solution used to calibrate the fuel cell;

B,C and D are constants characteristic of the fuel cell being used and of a housing of the fuel cell; and x is the temperature detected.

8. A method as claimed in claim 6, including calibrating the fuel cell with a wet standard.

9. A method as claimed in claim 6, wherein the fuel cell is heated.

10. A method as claimed in claim 9, wherein the heater is switched-off when or before a sample is supplied to the fuel cell.

11. A method of calibrating a breath testing apparatus having a fuel cell including supplying a wet standard and compensating a resultant output of the fuel cell in accordance with the temperature of the fuel cell or a housing containing the fuel cell.

\* \* \* \* \*